(12) United States Patent
Mayaudon et al.

(10) Patent No.: US 10,358,627 B2
(45) Date of Patent: *Jul. 23, 2019

(54) MEDIUM AND METHODS FOR THE STORAGE OF PLATELETS

(71) Applicant: Fenwal, Inc., Lake Zurich, IL (US)

(72) Inventors: Veronique Mayaudon, Gognies-Chaussee (BE); Jean-Marc Payrat, Baulers (BE)

(73) Assignee: FENWAL, INC., Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/462,151

(22) Filed: Aug. 18, 2014

(65) Prior Publication Data

US 2015/0004694 A1   Jan. 1, 2015

Related U.S. Application Data

(63) Continuation of application No. 12/338,574, filed on Dec. 18, 2008, now Pat. No. 8,835,104.

(60) Provisional application No. 61/096,581, filed on Sep. 12, 2008, provisional application No. 61/031,616, filed on Feb. 26, 2008, provisional application No. 61/015,529, filed on Dec. 20, 2007.

(51) Int. Cl.
  *A01N 1/02* (2006.01)
  *C12N 5/078* (2010.01)
  *A61K 35/19* (2015.01)

(52) U.S. Cl.
  CPC ............ *C12N 5/0644* (2013.01); *A01N 1/02* (2013.01); *A01N 1/0226* (2013.01); *A61K 35/19* (2013.01)

(58) Field of Classification Search
  CPC ........ A01N 1/02; A01N 1/0226; A61K 35/19; C12N 5/0644
  See application file for complete search history.

(56) References Cited

U.S. PATENT DOCUMENTS

| | | |
|---|---|---|
| 2,786,014 A | 3/1957 | Tullis |
| 3,629,071 A | 12/1971 | Sekhar |
| 4,054,488 A | 10/1977 | Marbach |
| 4,061,537 A | 12/1977 | Seiler |
| 4,124,598 A | 11/1978 | Hearst et al. |
| 4,314,025 A | 2/1982 | McCue |
| 4,405,719 A | 9/1983 | Crews et al. |
| 4,447,415 A | 5/1984 | Rock et al. |
| 4,455,299 A | 6/1984 | Grode |
| 4,572,899 A | 2/1986 | Walker et al. |
| 4,585,735 A | 4/1986 | Meryman et al. |
| 4,608,255 A | 8/1986 | Kahn et al. |
| 4,626,431 A | 12/1986 | Batchelor et al. |
| 4,626,432 A | 12/1986 | Hyde et al. |
| 4,695,460 A | 9/1987 | Holme |
| 4,702,352 A | 10/1987 | Ingram |
| RE32,874 E | 2/1989 | Rock et al. |
| 4,828,976 A | 5/1989 | Murphy |
| 4,925,665 A | 5/1990 | Murphy |
| 4,946,648 A | 8/1990 | Dichtelmuller et al. |
| 4,961,928 A | 10/1990 | Holme |
| 4,980,277 A | 12/1990 | Junnila |
| 4,992,363 A | 2/1991 | Murphy |
| 4,994,367 A | 2/1991 | Bode et al. |
| 5,089,146 A | 2/1992 | Carmen et al. |
| 5,133,932 A | 7/1992 | Gunn et al. |
| 5,147,290 A | 9/1992 | Jonsson |
| 5,152,905 A | 10/1992 | Pall et al. |
| 5,213,813 A | 5/1993 | Kornecki et al. |
| 5,234,808 A | 8/1993 | Murphy |
| 5,236,716 A | 8/1993 | Carmen et al. |
| 5,248,506 A | 9/1993 | Holme et al. |
| 5,281,392 A | 1/1994 | Rubinstein et al. |
| 5,300,019 A | 4/1994 | Bischo et al. |
| 5,344,752 A | 9/1994 | Murphy |
| 5,358,844 A | 10/1994 | Stossel et al. |
| 5,376,524 A | 12/1994 | Murphy et al. |
| 5,378,601 A | 1/1995 | Gepner-Puszkin |
| 5,399,268 A | 3/1995 | Pall et al. |
| 5,427,695 A | 6/1995 | Brown |
| 5,439,570 A | 8/1995 | Sessler et al. |
| 5,459,030 A | 10/1995 | Lin et al. |
| 5,462,733 A | 10/1995 | Edelson et al. |
| 5,466,573 A | 10/1995 | Murphy et al. |
| 5,474,891 A | 12/1995 | Murphy |
| 5,480,773 A | 1/1996 | Ogata et al. |
| 5,482,828 A | 1/1996 | Lin et al. |

(Continued)

FOREIGN PATENT DOCUMENTS

| | | |
|---|---|---|
| DE | 3804965 A1 | 8/1989 |
| DE | 43 30 213 A1 | 3/1995 |
| DE | 195 19886 A1 | 12/1995 |
| DE | 691 23 569 T2 | 6/1997 |
| DE | 699 12 457 T2 | 8/2004 |
| EP | 0 108 588 B1 | 6/1989 |
| EP | 0 237 863 B1 | 4/1990 |
| EP | 0510 185 B1 | 12/1996 |
| EP | 0 754 461 A2 | 1/1997 |
| EP | 0 853 881 A2 | 7/1998 |
| EP | 0 853 882 A2 | 7/1998 |
| EP | 1 109 447 B1 | 10/2003 |
| EP | 1 435 241 A1 | 7/2004 |
| EP | 1 736 051 A2 | 12/2006 |
| FR | 2 529 787 | 2/1984 |
| FR | 2 663 505 | 12/1991 |

(Continued)

OTHER PUBLICATIONS

Mohan C. A Calbiochem(R) brochure entitled "Buffers: A guide for the preparation and use of buffers in biological systems", 2006, on the web at https://www.med.unc.edu/pharm/sondeklab/files/resource-files/protein-purification-handbooks/buffers_calbiochem.pdf , Total pp. 1-38. (Year: 2006).*

(Continued)

*Primary Examiner* — Satyendra K Singh
(74) *Attorney, Agent, or Firm* — Cook Alex Ltd.

(57) ABSTRACT

Synthetic storage media are disclosed for use in the processing and the storing of platelets. The storage media includes a platelet storage solution and less than 20 percent plasma to preserve platelet function after at least 7 days of storage.

2 Claims, 14 Drawing Sheets

(56) References Cited

U.S. PATENT DOCUMENTS

| | | |
|---|---|---|
| 5,484,803 A | 1/1996 | Richter |
| 5,487,971 A | 1/1996 | Holme et al. |
| 5,511,558 A | 4/1996 | Shepard |
| 5,536,238 A | 7/1996 | Bischof |
| 5,538,894 A | 7/1996 | Patscheke et al. |
| 5,554,527 A | 9/1996 | Fickenscher |
| 5,569,579 A * | 10/1996 | Murphy ............ A01N 1/0226 424/532 |
| 5,601,972 A | 2/1997 | Meryman |
| 5,622,867 A | 4/1997 | Livesey et al. |
| 5,629,145 A | 5/1997 | Meryman |
| 5,651,966 A | 7/1997 | Read et al. |
| 5,667,963 A | 8/1997 | Smith et al. |
| 5,712,085 A | 1/1998 | Wollowitz et al. |
| 5,712,086 A | 1/1998 | Horowitz et al. |
| 5,753,428 A | 5/1998 | Yuasa et al. |
| 5,762,867 A | 6/1998 | D'Silva |
| 5,769,839 A | 6/1998 | Carmen et al. |
| 5,834,418 A | 11/1998 | Brazeau |
| 5,868,695 A | 2/1999 | Wolf, Jr. |
| 5,871,459 A | 2/1999 | Muller |
| 5,871,900 A | 2/1999 | Wollowitz |
| 5,899,874 A | 5/1999 | Jonsson |
| 5,906,915 A | 5/1999 | Payrat et al. |
| 5,908,742 A | 6/1999 | Lin et al. |
| 5,922,278 A | 7/1999 | Chapman et al. |
| 5,935,092 A | 8/1999 | Sun et al. |
| 5,951,509 A | 9/1999 | Morris |
| 5,965,349 A | 10/1999 | Lin et al. |
| 6,004,742 A | 12/1999 | Wollowitz et al. |
| 6,017,691 A | 1/2000 | Wollowitz et al. |
| 6,063,624 A | 5/2000 | Kandler et al. |
| 6,114,130 A | 9/2000 | Veriac et al. |
| 6,193,891 B1 | 2/2001 | Kent et al. |
| 6,194,139 B1 | 2/2001 | Wollowitz et al. |
| 6,218,100 B1 | 4/2001 | Wollowitz et al. |
| 6,221,669 B1 | 4/2001 | Livesey et al. |
| 6,251,580 B1 | 6/2001 | Lin et al. |
| 6,277,556 B1 | 8/2001 | Grode et al. |
| 6,277,577 B1 | 8/2001 | Rossau et al. |
| 6,326,197 B1 | 12/2001 | Kandler et al. |
| 6,413,713 B1 | 7/2002 | Serebrennikov et al. |
| 6,482,585 B2 | 11/2002 | Dottori |
| 6,492,103 B1 | 12/2002 | Taylor et al. |
| 6,544,727 B1 | 4/2003 | Hei |
| 6,548,241 B1 | 4/2003 | McBurney et al. |
| 6,566,046 B2 | 5/2003 | Lin et al. |
| 6,653,062 B1 | 11/2003 | DePablo et al. |
| 6,723,497 B2 | 4/2004 | Wolkers |
| 6,743,575 B2 | 6/2004 | Wiggins et al. |
| 6,790,603 B2 | 9/2004 | Ericson et al. |
| 6,828,090 B2 | 12/2004 | Lucas et al. |
| 6,866,992 B2 | 3/2005 | Lin et al. |
| 6,913,932 B2 | 7/2005 | Maples |
| 6,919,172 B2 | 7/2005 | DePablo et al. |
| 6,936,413 B1 | 8/2005 | Bischof et al. |
| 6,960,428 B2 | 11/2005 | Dottori |
| 6,994,954 B2 | 2/2006 | Taylor |
| 7,011,938 B2 | 3/2006 | Macey |
| 7,037,642 B2 | 5/2006 | Hei |
| 7,083,910 B2 | 8/2006 | Lucas et al. |
| 7,169,606 B2 | 1/2007 | DePablo et al. |
| 7,202,020 B2 | 4/2007 | Lucas et al. |
| 7,220,747 B2 | 5/2007 | Dumont et al. |
| 7,241,282 B2 | 7/2007 | Stossel |
| 7,255,983 B2 | 8/2007 | Steen |
| 7,264,608 B2 | 9/2007 | Bischof et al. |
| 8,835,104 B2 * | 9/2014 | Mayaudon ............ A01N 1/02 424/93.72 |
| 2002/0034722 A1 | 3/2002 | Ericson et al. |
| 2002/0045228 A1 | 4/2002 | Hei |
| 2002/0104808 A1 | 8/2002 | Blasetti et al. |
| 2002/0131958 A1 | 9/2002 | Chapman et al. |
| 2002/0146400 A1 | 10/2002 | Cincotta |
| 2002/0164795 A1 | 11/2002 | Gen |
| 2003/0186213 A1 | 10/2003 | McBurney et al. |
| 2003/0215781 A1 | 11/2003 | DeGroot et al. |
| 2003/0215785 A1 | 11/2003 | Goodrich et al. |
| 2004/0023201 A9 | 2/2004 | McBurney et al. |
| 2004/0038997 A1 | 2/2004 | Macey |
| 2004/0132207 A1 | 7/2004 | Arima et al. |
| 2004/0185544 A9 | 9/2004 | Hei |
| 2004/0209236 A1 | 10/2004 | DePablo et al. |
| 2004/0229205 A1 | 11/2004 | Ericson et al. |
| 2005/0074743 A1 | 4/2005 | Purmal et al. |
| 2005/0233302 A1 | 10/2005 | Hess et al. |
| 2005/0256443 A1 | 11/2005 | Bischof et al. |
| 2006/0177811 A1 | 8/2006 | Sehgel et al. |
| 2007/0031812 A1 | 2/2007 | Holme |
| 2007/0190636 A1 | 8/2007 | Hassanein et al. |
| 2008/0044803 A1 | 2/2008 | Gyonggossy-Issa |

FOREIGN PATENT DOCUMENTS

| | | |
|---|---|---|
| FR | 2 672 129 | 7/1992 |
| FR | 2 691 911 | 12/1993 |
| FR | 2 782 166 | 2/2000 |
| JP | 8165245 A | 6/1996 |
| WO | WO 87/05468 | 9/1987 |
| WO | WO 92/08349 | 5/1992 |
| WO | WO/09208349 A1 | 5/1992 |
| WO | WO 92/18136 | 10/1992 |
| WO | WO/0416099 A1 | 1/1994 |
| WO | WO/09603139 A1 | 2/1996 |
| WO | WO 96/13158 | 5/1996 |
| WO | WO 98/56247 | 12/1998 |
| WO | WO 00/11946 | 3/2000 |
| WO | WO 01/45502 | 6/2001 |
| WO | WO 02/23988 | 3/2002 |
| WO | WO 02/43485 | 6/2002 |
| WO | WO 02/087560 | 11/2002 |
| WO | WO 03/000052 | 1/2003 |
| WO | WO 03/049634 | 6/2003 |
| WO | WO 03/049784 | 6/2003 |
| WO | WO 03/090794 | 11/2003 |
| WO | WO 2004/112477 | 12/2004 |
| WO | WO 2005/013689 | 2/2005 |
| WO | WO 2006/012615 | 2/2006 |
| WO | WO 2006/044790 | 4/2006 |
| WO | WO 2006/076401 | 7/2006 |
| WO | WO 2006/088455 | 8/2006 |
| WO | WO 2007/003382 | 1/2007 |
| WO | WO 2007/047687 | 4/2007 |
| WO | WO/070647687 A2 | 4/2007 |
| WO | WO/07054160 A2 | 5/2007 |
| WO | WO 2007/067482 | 6/2007 |
| WO | WO 07/082916 A1 | 7/2007 |
| WO | WO 02/000827917 A2 | 3/2008 |
| WO | WO 08/037481 A2 | 4/2008 |
| WO | WO 08/048228 A2 | 4/2008 |
| WO | WO 2008/089776 | 7/2008 |
| WO | WO 08/113017 A2 | 9/2008 |

OTHER PUBLICATIONS

Petronilli, et al., Modulation of the Mitochondria cyclosporin-A Sensitive Permeability Transition Pore, 1993, J. Biol. Chem, vol. 208 pp. 1011-1016.

Gulliksson, et al., Storage of Platelets in Additive Solutions, Effects of Phosphate 2000, Vox Sanguinis, vol. 78, pp. 176-184.

Siliprandi, et al., Stimuation of Oxidation of Mitochondrial Fatty Acids and Acetate by acetyl carnitine 1965, Biochem J., vol. 96, pp. 777-780.

Hiriyama, et al., Storage of Platelets in a Novel Additive Solution (M-sol) which is Prepared by Mixing Solutions that are not Especially Approved for Platelet Storage, Jun. 2007, Transfusion, vol. 47, pp. 960-965.

Van Rhenen, et al., Therapeutic Efficacy of Pooled Buffy-coat Platelet Components Prepared and Stored With a Platelet Additive Solution, Transfus Med. Aug. 2004 14(4): 289-95.

(56) References Cited

OTHER PUBLICATIONS

Diedrich, et al., In Vitro and in Vivo Effects of Potassium and Magnesium on Storage up to 7 days of Apheresis Platelet Concentrates in Platelet Additive Solution. Vox Sang, Feb. 2008 '94(2): 96-102. Epub Nov. 22, 2007.

Kerkhoffs, et al., A Muticenter Randomized Study of the Efficacy of Transfusions With Platelets Stored in Platelet Additive Solution II Versus Plasma Blood 108: 3210-3215, published online Jul. 6, 2006.

Vetlesen, et al., Platelet Activation and Residual Activation Potential During Storage of Hyperconcentrated Platelet Products in Two Different Platelet Additive Solutions, Transfusion, Aug. 2005; 45(8): 1349-55.

Sweeney J, et al., Storage of Platelet-rich Plasma-Derived Platelet Concentrate Pools in Plasma and Additive Solution, Transfusion, May 2006, 46(5):835-40.

Holme, et al., Blood Collection and Components, The Expression of P-Selectin During Collection, Processing, and Storage of Platelet Concentrates: Relationship to Loss of In Vivo Viability, Transfusion 1997; 37;12-17.

Holme, et al., A Multi-Laboratory Evaluation of In Vitro Platelet Assays: the Tests for Extent of Shape Change and Response to Hypotonic Shock, Transfusion 1998; 38:31-40.

Bertolini, et al., A Multicenter Evaluation of Reproducibility of Swirling in Platelet Concentrates, Transfusion, 1994; 34:796-801.

Shimizu, T., et al., "First Autoclave-Sterilized Platelet-Additive Solution Containing Glucose with a Physiological pH for the Preparation of Plasma-Poor Platelet Concentrates", Vox Sang, vol. 62, 1992, pp. 87-93.

Gulliksson, Hans, "Defining the Optimal Storage Conditions for the Long-Term Storage of Platelets", Transfusion Medicine Reviews, vol. 17, No. 3, Jul. 2003, pp. 209-215.

Murphy, S., et al., "Amino Acid Metabolism During Platelet Storage for Transfusion", British Journal of Haematology, Jan. 1, 1992, pp. 585-590.

Shimizu, T., et al., "Roles of acetate and phosphate in the successful storage of platelet concentrates prepared with an acetate-containing additive solution", Transfusion, vol. 33, No. 4, Jan. 1, 1993, pp. 304-310.

Sweeney, J., et al., "L-Carnitine and Its Possible Role in Red Cell and Platelet Storage", Transfusion Medicine Reviews, vol. 18, No. 1, Jan. 2004, pp. 58-65.

EP Communication dated Apr. 16, 2012 regarding European Search Report and Annex for EP Application No. 08 022161.

Hirayama, J., et al., "Storage of Platelets in 30 percent plasma and 70 percent M-sol additive solution", Transfusion, vol. 48, Mar. 2008, pp. 567-568.

Azuma, H., et al., "Reduction in adverse reactions to platelets by the removal of plasma supernatant and resuspension in a new additive solution", Transfusion, vol. 49, Feb. 2009, pp. 214-218.

Hirayama, J., et al., "Storage of platelets in a novel additive solution (M-sol), which is prepared by mixing solutions approved for clinical use that are not especially for platelet storage", Transfusion, vol. 47, Jun. 2007, pp. 960-965.

Murphy, et al., "Platelet Storage for Transfussion in Synthetic Media: Further Optimization of Ingredients and Definition of Their Roles", Blood, vol. 86, No. 10, pp. 3951-3960 (1995).

\* cited by examiner

Fig. 3

| N=8 per arm | Day 1 | Volume (ml) | Platelet Count (x10$^9$/Liter) | Platelet content (x10$^9$/unit) | Plasma ratio in PC (%) | WBC (x10$^6$/unit) |
|---|---|---|---|---|---|---|
|  | Acceptance criteria | - | - | - | 17 – 23 (Test arms) | <1,0 |
| Control | Plasma 100% | 308 ± 5 | 930 ± 76 | 286 ± 20 | 100 ± - | < 0,2 |
| Test arm 1 | Plasma 20%/ InterSol | 294 ± 4 | 893 ± 76 | 262 ± 19 | 19,0 ± 0,6 | < 0,2 |
| Test arm 2 | Plasma 20%/ PSM 1 | 308 ± 3 | 815 ± 42 | 251 ± 13 | 18,7 ± 0,7 | < 0,2 |
| Test arm 3 | Plasma 20%/ PSM 2 | 300 ± 4 | 912 ± 67 | 273 ± 18 | 19,8 ± 0,8 | < 0,2 |
| Test arm 4 | Plasma 20%/ PSM 3 | 300 ± 4 | 908 ± 62 | 272 ± 17 | 19,9 ± 0,7 | < 0,2 |

MEDIUM AND METHODS FOR THE STORAGE OF PLATELETS

This application is a continuation of U.S. Ser. No. 12/338,574 filed Dec. 18, 2008, which claims the benefit of U.S. Provisional Patent Application No. 61/015,529, filed Dec. 20, 2007, U.S. Provisional Patent Application No. 61/031,616, filed Feb. 26, 2008, and U.S. Provisional Patent Application No. 61/096,581 filed Sep. 12, 2008, all of which are incorporated by reference in their entirety.

FIELD OF THE DISCLOSURE

The present disclosure relates to storage media for blood components such as blood platelets, which optimize energy metabolism of platelets stored in vitro to preserve and prolong platelet functionality. More particularly, the present disclosure relates to storage media that includes a synthetic storage solution and plasma, where a reduced amount of plasma may be utilized.

DESCRIPTION OF RELATED ART

Methods of separating platelets from whole blood as well as methods for storing platelets for later transfusion to a patient are well known. Various synthetic media useful for the storage of platelets are disclosed in U.S. Pat. No. 5,569,579 (Murphy) and U.S. Pat. No. 5,908,742 (Lin et al.), which are incorporated herein by reference. The platelets may be stored in a platelet storage medium that includes an aqueous storage solution and some amount of plasma.

BACKGROUND

Whole blood is made up of various cellular components such as red cells, white cells and platelets suspended in its liquid component, plasma. Whole blood can be separated into its constituent components (cellular or liquid), and the desired separated component can be administered to a patient in need of that particular component. For example, platelets can be removed from the whole blood of a healthy donor, collected, and later administered to a cancer patient, whose ability to "make" platelets has been compromised by chemotherapy or radiation treatment.

Commonly, platelets are collected by introducing whole blood into a centrifuge chamber wherein the whole blood is separated into its constituent components, including platelets, based on the densities of the different components. In the separation of platelets, sometimes referred to as plateletpheresis, the platelets are often concentrated to form a layer of packed platelets with some residual plasma (hereinafter "platelet concentrate" or "PC"). Platelets may also be derived from buffy coats obtained from manually collected units of whole blood. A plurality of buffy coats are typically pooled to provide an amount or dose of platelets suitable for transfusion. The platelet product is typically stored until needed for transfusion to a patient. For storage, the platelet product is typically resuspended in a liquid medium, such as plasma and/or a synthetic storage solution.

For the stored platelets to be suitable for later administration they must substantially retain their viability and platelet function. A number of interrelated factors may affect platelet viability and function during storage. Some of these factors include the anticoagulant used for blood collection, the method used to prepare the platelets, the type of storage container used, and the medium in which the platelets are stored.

Currently, platelets may be stored for five or even seven days at 22° C. After five days, however, platelet function may become impaired. In addition to storage time, other storage conditions have been shown to affect platelet metabolism and function including pH, storage temperature, total platelet count, plasma volume, and agitation during storage.

In order to maintain viability, platelets must generate new adenosine triphosphate (ATP) continuously to meet their energy needs. As shown in FIG. 1 platelets use two metabolic pathways to generate ATP: (a) anaerobic glycolysis followed by lactic acid fermentation or (b) glycolysis followed by oxidative phosphorylation. Glycolysis results in one mole of glucose being converted to 2 moles of pyruvate, and two moles of ATP. The pyruvate can then undergo lactic acid fermentation also called anaerobic glycolysis. Although no additional ATP is produced in lactic acid fermentation, the conversion of pyruvate to lactic acid regenerates $NAD^+$ and allows glycolysis to continue generating at least a small amount of ATP from the metabolism of glucose. Because lactic acid fermentation, which can negatively affect the pH of the medium and platelets stored therein, is stimulated by the absence of oxygen, platelets are typically stored in containers permeable to oxygen to promote oxidative phosphorylation and suppress lactic acid formation.

In oxidative phosphorylation, pyruvate, fatty acid or amino acids are converted to $CO_2$ and water in the citric acid cycle. This pathway requires the presence of an adequate supply of oxygen. Glycolysis followed by oxidative phosphorylation produces 36 moles of ATP per mole of glucose and therefore is much more efficient than glycolysis followed by lactic acid fermentation.

However, rather than utilizing oxidative phosphorylation exclusively, the platelets continue to produce lactic acid through anaerobic glycolysis. Therefore, even in the presence of adequate amounts of oxygen and when stored in media containing glucose, (media such as plasma and certain synthetic storage solutions) the utilization by platelets of glycolysis coupled with lactic acid fermentation for energy production results in the concentration of lactic acid increasing over time. As noted above, the increase in lactic acid gradually acidifies the storage media. This acidification of the media alters platelet physiology and morphology such that when the pH of the media drops below about 6 the platelets may be considered nonviable. Even drops in pH that are too small to render platelets nonviable have been observed to cause decreases in the total amount of ATP. These reductions in ATP affect platelet function as ATP plays a role in for platelet adhesion and platelet aggregation. Consequently, it would be desirable to provide a storage medium for platelets that results in the prevention and/or delay of this decrease in pH.

A variety of tests have been developed which attempt to determine the quality of stored platelets and the in vivo viability of those platelets when transfused to a patient. For instance, the percentage of platelets that maintain a discoid shape (the ESC assay) and the percentage of platelets that respond appropriately to hypotonic shock (HSR assay) are two assays which are thought to correlate well with viability of stored platelets. The ESC assay measures the percentage of platelets in a sample which have discoid morphology.

The results of the HSR (Hypotonic Shock Response) assay are often considered to correlate strongly with the in vivo effectiveness of platelets when they are introduced into an individual. This assay measures the ability of platelets to recover a discoid shape after swelling in response to a hypotonic environment. Higher scores on either the HSR or ESC assay appear to correlate with increased viability of the platelets when transfused to patients. For example, an HSR assay result of about 40% or less may indicate an ineffective platelet population. The methods and uses of the HSR and ESC assays are described in more detail by Holme et al. Transfusion, January 1998; 38:31-40, which is incorporated by reference herein.

Another shape based assay is the so called "swirling assay" which has also been used as a measure of the quality of platelet concentrates. The swirling assay is based on the ability of discoid platelets to reflect light, producing a shimmering phenomenon. As described by Bertolini and Murphy, Transfusion 1994; 34:796-801 and Transfusion 1996: 36:128-132 and incorporated herein by reference, platelet samples scoring positive in a swirling assay are believed to be of higher quality than samples scoring intermediate or negative for swirling.

The presence of the glycoprotein P-selectin on the surface of platelets is also used to characterize the viability of platelets upon transfusion with the presence of P-selectin believed to indicate a loss of viability. As described by Holme et al. Transfusion 1997; 37:12-17 and incorporated herein by reference, Platelets undergo a shape change transforming from disc shaped to sphere shaped upon platelet activation. This activation is thought to involve the secretion of β-thromboglobulin from the alpha granules resulting in the appearance of P-selectin on the surface of the platelets. Antibodies directed against P-selectin, such as the monoclonal antibody CD62P, are used to detect the presence of P-selectin on the surface of platelets and have been used as a marker of platelet activation and a decreased viability of the platelets upon transfusion.

Another marker of the quality of platelets is extracellular levels of lactate dehydrogenase. Lactate dehydrogenase is an intracellular enzyme and therefore higher extracellular levels of lactate dehydrogenase are thought to reflect increased levels of platelet lysis.

A number of approaches for the storage of platelets for transfusion have been described. Although plasma is effective for storage of platelets, it may not be the ideal medium for platelet storage because plasma itself is a valuable blood component that can be used or further processed for use in the treatment of patients with other disorders. Accordingly, synthetic aqueous solutions have been developed to preserve plasma for other uses and still provide a suitable environment for stored platelets. Such solutions may be "stand alone" solutions or may be used in combination with some amount of plasma.

InterSol®, a commercially available platelet storage medium is generally described in U.S. Pat. No. 5,908,742 which is incorporated herein in its entirety. InterSol® contains sodium citrate, sodium acetate, sodium phosphate and adjusted to isoosmolarity with sodium chloride. A typical formulation of InterSol® contains 21.5 mM (3.05 g/L) dibasic sodium phosphate anhydrous ($Na_2HPO_4$), 6.7 mM (1.05 g/L) monobasic sodium phosphate ($NaH_2PO_4.2H_2O$), 10.8 mM (3.18 g/L) sodium citrate $2H_2O$, 32.5 mM (4.42 g/L) sodium acetate $3H_2O$, and 77.3 mM (4.52 g/L) sodium chloride. The InterSol® solution is approximately isoosmolar (about 300 mOsm/L) with platelets and plasma, and has a pH of approximately 7.2. In certain applications (such as, but not limited to, inactivation of pathogens in platelets) InterSol® may be used in combination with plasma ratio of InterSol®/plasma ratio approximately 70%130% to 60%/40%. Phosphate buffer in InterSol® stabilizes the pH of the solution during platelet storage.

While InterSol® has worked satisfactorily in the preservation of blood platelets, further improvements to the storage time and in vivo viability of platelets would be desirable. For example, as noted above, it would be desirable to develop a platelet storage media that reduces platelet utilization of lactic acid fermentation and thus slows the drop in pH that typically occurs during platelet storage. It would also be desirable to develop a synthetic storage media that requires a reduced amount of plasma (less than approximately 30%) in the synthetic storage media for the storage of platelets. It would also be desirable to provide a platelet storage media with a lower concentration of phosphate and a sufficient supply of nutrients to substantially meet the energy needs of the platelets during storage while maintaining a pH between about 6.4 and about 7.4.

SUMMARY

In one aspect, the present disclosure is directed to an aqueous solution for the storage of platelets. The solution may contain from about 45 to about 120 mM sodium chloride, from about 5 to about 15 mM sodium citrate, from about 20 to about 40 mM sodium acetate, from about 0.05 to about 12 mM phosphate, from about 0.05 to about 3 mM magnesium ion and a nutrient for the platelets.

In another aspect, the subject matter of the disclosure is directed to a platelet product. The platelet product includes platelets, from about 80-100% of an aqueous solution. The aqueous solution includes from about 45 to about 120 mM sodium chloride, from about 5 to about 15 mM sodium citrate, from about 20 to about 40 mM sodium acetate, from about 0.05 to about 10 mM sodium phosphate, from about 0.05 to about 3 mM magnesium ion, from about 0.05 to about 10 mM potassium chloride, from about 0.5 to about 20 mM glucose. The platelet product also includes up to about 20% plasma.

In another aspect, the present disclosure is directed to a method of storing platelets, which includes providing an amount of platelets, combining the platelets with a volume of an aqueous solution where the solution may include from about 45 to about 120 mM sodium chloride, from about 5 to about 15 mM sodium citrate, from about 20 to about 40 mM sodium acetate, from about 0.05 to about 12 mM phosphate, from about 0.05 to about 3 mM magnesium ion, a nutrient and a selected volume of plasma wherein the volume of plasma is less than 40% of the combined volume of platelets, plasma and solution.

BRIEF DESCRIPTION OF THE DRAWINGS

FIG. 3 is a table setting forth on day 1 the composition of the storage media, the platelet volumes in milliliter, platelet count ($10^9$/Liter) and platelet content per unit ($10^9$/unit), the plasma ratio in the platelet concentrate as a percentage of total volume, and white blood cell count (WBC $10^6$/unit) for the indicated arms of a study.

DESCRIPTION OF THE ILLUSTRATED EMBODIMENTS

Figure 1:
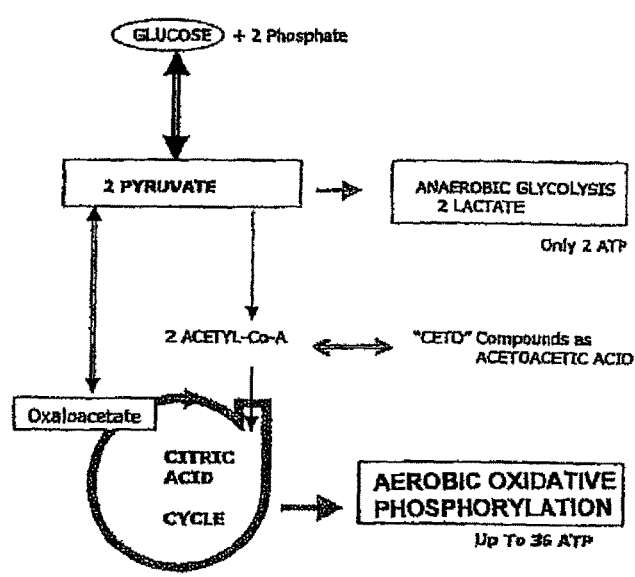
FIG. 1 is a representation of the glycolic and oxidative phosphorylation pathways for ATP production.

The embodiments disclosed herein are for the purpose of providing a general description of the storage media and methods and apparatus for storing blood components that are the subject of this disclosure. These embodiments are only exemplary, and may be embodied in various forms. Therefore, specific details disclosed herein are not to be interpreted as limiting the subject matter of the invention which is set forth in the accompanying claims.

The platelet storage media described herein include at least an aqueous solution and, in preferred embodiments, some amount of plasma. Platelet products described herein include the platelet storage media (platelet storage solution and plasma) and the platelets stored therein. Preferably the amount of plasma that makes up the storage media is "reduced". For example, less than about 40% of plasma may be utilized, more preferably less than about 20%, and typically between about 10%-20%, and even less than 10%.

It is presently believed and understood that platelet storage media described herein promote ATP production through the oxidative phosphorylation pathway over ATP production through anaerobic glycolysis, thereby limiting lactic acid formation and consequently, a decrease in the pH of the medium. Accordingly, platelets stored in the platelet storage media described herein exhibit properties such as response to hypotonic shock, levels of P-selectin, morphology etc. that are typically at least as good or better than platelets stored in plasma or other storage media.

In one embodiment, a platelet storage medium is provided that includes an aqueous storage solution that itself includes one or more nutrients and buffer(s) in a salt solution. The buffer which may be a phosphate buffer may include a lower concentration (as compared to InterSol® or other storage solution or media) of phosphate in the platelet storage medium.

Thus, an embodiment of the aqueous storage solution described herein may include 45-120 mM sodium chloride, 5-15 mM sodium citrate, 20-40 mM sodium acetate, 0.5-12 mM phosphate buffer, 0.05-3 mM magnesium ion, and 0.5-20 mM glucose, with the initial pH of the complete storage media ranging from 6.8-7.3. Optionally, 0.05-3 mM calcium chloride and/or 0.05-10 mM potassium chloride may also be present in synthetic platelet storage solution. Also optionally, 0.1-10 µM of a naturally occurring ester of L-carnitine (e.g. acetyl-L-carnitine) may be added to a platelet storage media to further promote oxidative phosphorylation.

In a more specific embodiment the sodium chloride may be present from about 50 mM to about 110 mM. More particularly, the sodium chloride may be present from about 58 mM to about 90 mM, or from about 65 mM to about 80 mM. Also, more preferably, the sodium citrate may be present from about 7 mM to about 13 mM, and more typically from about 9 mM to about 12 mM. As set forth above, the storage solution may also include an amount of sodium acetate. In one embodiment the sodium acetate may be present from about 24 mM to about 36 mM, and more preferably from about 28 mM to about 33 mM.

Preferably, a buffer such as phosphate is also included in the storage solution described herein. In one embodiment, phosphate may be present from about 3 mM to about 11 mM, and more typically from about 6 mM to about 10 mM. Examples of sources of phosphate include (but are not limited to) sodium phosphate and/or potassium phosphate. In addition, the sodium phosphate and potassium phosphate used may include various forms of phosphate such as either or both monobasic and dibasic forms of phosphate. For example, a phosphate buffer having a phosphate concentration of 9.4 mM may contain approximately 7.2 mM (1.017 g/L) dibasic sodium phosphate anhydrous ($Na_2HPO_4$) and 2.2 (0.350 g/L) mM monobasic sodium phosphate dihydrate ($NaH_2PO_4.2H_2O$).

It is understood that the conversion of 1 mole of glucose to 2 moles of pyruvate requires two (2) moles of inorganic phosphate. Consequently, the metabolism of glucose to pyruvate, the step preceding oxidative phosphorylation, requires the presence of phosphate. However, high levels of phosphate may alter the permeability of the mitochondrial membrane and reduce the likelihood of maintaining intact platelet mitochondria. As the citric acid cycle of oxidative phosphorylation takes place in the mitochondria, it is desirable to maintain intact mitochondria to optimize platelet utilization of oxidative phosphorylation during storage in order to maintain a stable pH in the medium and adequate levels of ATP in the platelets.

In platelets stored in plasma, oxidative phosphorylation is active and the mean lactic acid concentration is about 18 mEq/L. Therefore, a synthetic storage medium which has a phosphate concentration of less than approximately 10 mM and promotes oxidative phosphorylation during platelet storage should be capable of buffering the $H^+$ produced from the fraction of pyruvate produced by glycolysis that undergoes lactic acid fermentation. Consequently, the phosphate concentration of the synthetic storage solution described herein is preferably below 10 mM in order to maintain intact platelet mitochondria with normal membrane permeability. For example, the addition of 300 ml of an aqueous solution with a phosphate concentration of about 9.4 mM is combined with a platelet concentrate in plasma to produce a suspension of platelets in a storage solution comprising 10% plasma, the final phosphate concentration will be approximately 15 mEq/L.

The storage solution disclosed herein may also be buffered by amino acids. The amino adds may be used as the primary buffering agents, or may be used in conjunction with other buffering agents such as phosphate. In one embodiment the amino acid, histidine may be used to buffer the storage solution. Thus, the storage solution may contain amino acids from about 1 mM to about 7 mM, or from about 2 mM to about 5 mM. More particularly, the storage solution may contain histidine from about 1 mM to about 7 mM, or from about 2 mM to about 5 mM.

The storage solution described herein may also include a selected concentration of magnesium ion. In one embodiment, magnesium ion may be present in the synthetic solution at concentrations close to plasma levels which will be about 3 mEq/l, (1.5 mM). Magnesium ion at high cytosolic (intercellular) concentrations appears to play a role in resealing of the mitochondria. [Petrolfini V, Cola C, Bernardi P, Modulation of the mitochondria cyclosporin A-sensitive permeability transition pore, J. Biol Chem 1993; 268; 1011-6.] Consequently, magnesium ion in the medium should maintain the optimal intercellular magnesium levels in the platelets and may promote oxidative phosphorylation in the platelets and in so doing help maintain the pH of the medium. Preferably, magnesium ion may be added either as a chloride or a sulfate salt. In one embodiment magnesium ion may be present from about 0.05 mM to about 4 mM. More typically, magnesium ion may be present from about 0.1 mM to about 3.5 mM, or from about 0.5 mM to about 3.0 mM, or from about 1.0 mM to about 2.5 mM. In one particular embodiment, magnesium ion may be present from about 1.4 mM to about 2.2 mM.

The storage solution described herein may also include a selected concentration of calcium ion. For example, calcium ion may be present in the aqueous solution. The presence of calcium ion in the medium may assist in maintaining intracellular magnesium ions. Stress can cause an influx of calcium into platelets, therefore to maintain free calcium in the complete storage medium, the synthetic storage media may initially contain about 0.5 mM to about 2.5 mM (1 to 5 mEq/) calcium ion. In one embodiment calcium ion may be present from about 0.05 mM to about 3 mM. More particularly, calcium ion may be present from about 0.4 mM to about 2.8 mM, or from about 0.6 mM to about 2.2 mM, or about 0.8 mM to about 1.2 mM.

The storage solution described herein may also include a selected concentration of potassium ion. The presence of potassium ion in the medium may assist in maintaining intracellular magnesium ion concentration. Potassium ion also appears to be involved in the transport of pyruvate across the mitochondria membrane for oxidative phosphorylation in the citric acid cycle (TCA cycle). Preferably, potassium ion may be present from about 1 mM to about 10 mM. More preferably, potassium ion may be present from about 2 mM to about 9 mM, or from about 3 mM to about 8 mM, or from about 4 mM to about 7 mM, or from about 4.5 mM to about 6.5 mM.

The storage solution described herein may include a combination of magnesium ion, calcium ion, and potassium ion, or any other subcombinations of these three ions may be present in the storage solution. Where the storage solution is separated into two compartments (described in detail below), such as a neutral buffered physiological compartment and a carbohydrate compartment, as shown, for example in FIG. 2, one or more of the magnesium ion, calcium ion, and potassium ion may be contained in either or both compartments.

In the storage solution and storage media described herein, a carbohydrate is preferably included as a nutrient source of intermediate metabolites for production of energy. Glucose and other carbohydrates such as sucrose are nutrients for the platelets and can provide an important source of energy for platelets in storage by being the primary source of intermediate metabolites for the production of energy in the citric acid cycle. However, it may be important to regulate the concentration carbohydrates in the storage medium, because an excess concentration of a carbohydrate such as glucose appears to cause increased lactic acid production. In one embodiment, the initial glucose concentration may be from about 0.5 mM to about 25 mM. More preferably, the initial glucose concentration may be from about 2 mM to about 22 mM. In some embodiments the initial glucose concentration may be from about 4 mM to about 20 mM. Preferably, the initial glucose concentration may be from about 6 mM to about 19 mM. In other embodiments the initial glucose concentration may be from about 10 mM to about 18 mM. Carbohydrates such as sucrose can be used either in place of glucose or in combination with glucose as primary energy sources.

Figure 2:
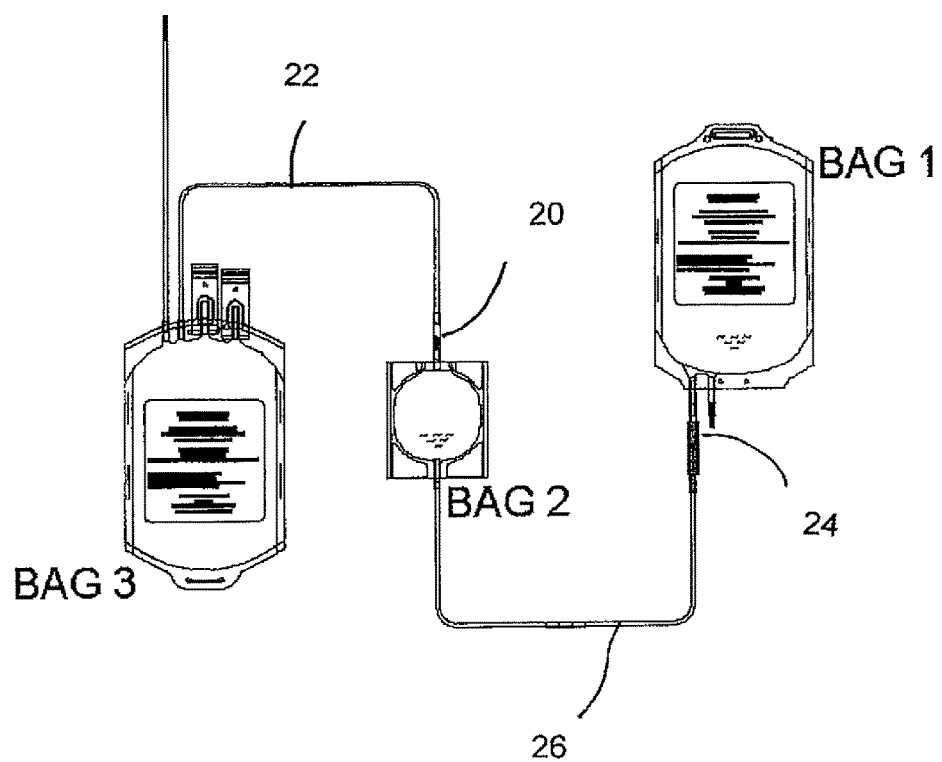
FIG. 2 illustrates an example of a container system for mixing the contents of the compartments of the synthetic storage solution and combining the solution with a platelet concentrate.

As noted above, the carbohydrate, for instance glucose, may be stored in a concentrated solution separately from the neutral buffered physiological salts. As shown in FIG. 2, the concentrated carbohydrate solution may also contain other salts such as the calcium, magnesium, potassium, or sodium salts or any possible subcombination of these salts to raise the osmolarity of the concentrated carbohydrate compartment such that it is close to that of the buffered physiological compartment (Bag 1). To allow heat sterilization, such as autoclaving of the glucose solution, the glucose solution should be acidic for example with a pH between from about 4 to about 6.

As an example of a concentrated carbohydrate solution, 25 ml of the concentrated glucose solution may be combined with 275 ml of the buffered salt solution to produce 300 ml of aqueous solution. In this example, the concentrated glucose solution is 40 g/l glucose which results in a concentration of 3.3 g/L or 0.32% weight/weight glucose in the final platelet mixture.

Carbohydrate such as glucose, and more particularly D-glucose (dextrose) may be added to the platelet storage medium on the processing day (day 1) and/or later during storage, for instance on day 3 or 4 of storage. Addition of carbohydrate subsequent to the processing day may allow lower initial concentrations of carbohydrate to be used in the storage buffer, and as the carbohydrate is metabolized during storage, additional carbohydrate may be added. In this manner, lower concentrations of the carbohydrates are present in the storage medium throughout platelet storage, which as discussed herein, helps to suppress the production of lactic acid.

Other nutrients may be substituted for or included with the glucose of the synthetic storage solution or storage media. For example, oxaloacetate may be present in the synthetic media or may be added to platelet suspension after the synthetic media has been added to a platelet rich fraction. To further reduce the risk of lactic acid build up during the storage of platelets, the synthetic storage media may be formulated such that it contains no or reduced amounts of glucose and similar carbohydrates, which generate pyruvate through glycolysis. In the absence of these carbohydrates pyruvate is not produced and consequently lactic acid is not produced. To maintain platelet ATP production in the absence of glucose or a similar carbohydrate, oxaloacetate may be added directly to synthetic storage media. Oxaloacetate is a four-carbon molecule found in the mitochondria that condenses with Acetyl Co-A to form the first reaction of the TCA cycle (citric acid cycle). As shown in FIG. 1, in the presence of glucose the oxaloacetate is produced from the oxidation of pyruvate. In the absence of glucose, the oxaloacetate cannot be produced from acetate as the conversion of pyruvate into acetic acid is irreversible. Consequently in the absence of glucose, oxaloacetate may be supplied to the stored platelets either directly or in the form of precursor amino acids such as aspartate.

The presence of oxaloacetate in the medium may allow the metabolism of acetyl Co-A and acetate to generate ATP. The presence of oxaloacetate therefore prevents the accumulation of acetate and the generation of "cetonic" compounds such as acetoacetic acid which can acidify the medium. As oxaloacetate is regenerated during each cycle of oxidative phosphorylation, the storage medium may contain approximately equimolar amounts of oxaloacetate and acetate. In some embodiments oxaloacetate may be present in the synthetic solution from about 10 mM to about 45 mM. More particularly, oxaloacetate may be present in the synthetic solution from about 20 mM to about 40 mM, or from about 24 mM to about 36 mM, or from about 28 mM to about 33 mM.

The storage solution and storage media generally disclosed herein may also include other components that promote oxidative phosphorylation. For example a naturally occurring ester of L-carnitine such as acetyl-L-carnitine may be included in the storage solution. Acetyl-L-carnitine in catalytic amounts has been shown to restore oxidative phosphorylation in aged mitochondria. Therefore, to preserve the mitochondria of stored platelets and promote oxidative phosphorylation of carbohydrates, naturally occurring esters of L-carnitine such as acetyl-L-carnitine may be present in the storage solution. The ester of L-carnitine may be present in the synthetic solution and/or may be added to the platelet suspension after the synthetic solution has been added to a platelet rich fraction. In still other, more specific embodiments, a naturally occurring esters of L-carnitine may be present in the storage solution from about 0.1 μM to about 10 μM. In some embodiments a naturally occurring esters of L-carnitine may be present in the storage solution from about 0.2 μM to about 8 μM. In some embodiments a naturally occurring ester(s) of L-carnitine may be present in the storage solution from about 0.5 μM to about 1.5 μM In addition to or as an alternative to the foregoing, the storage medium disclosed herein may further include other components that promote oxidative phosphorylation. An antioxidant may be added to the platelet storage medium or the composition that includes platelets and a storage medium. Examples of antioxidants include glutathione, selenium and the like. In some embodiments the antioxidant may be present in the synthetic solution from about 0.5 μM to about 3 mM. More particularly, the antioxidant may be present in the solution from about 1.0 μM to about 2 mM. In some embodiments glutathione, or its precursor N-acetylcysteine, and/or selenium alone or in combination may be present in the synthetic solution from about 0.5 μM to about 3 mM. More particularly, glutathione, or its precursor N-acetylcysteine, and/or selenium alone or in combination may be present in the synthetic solution from about 1.0 μM to about 2 mM. The antioxidants described herein may be included or added to the storage solutions and platelet storage media described herein as well as to known storage solutions such as Intersol® and media that include Intersol®.

To further promote oxidative phosphorylation, the synthetic storage medium or platelets in a storage medium disclosed herein may include other components that may stabilize membranes. For example, a phospholipid or a mixture or phospholipids may be included in the storage solution. In some embodiments, phospholipids may be present in the storage solution from about 0.1 mg/ml to about 7.5 mg/ml, and more typically from about 0.25 mg/ml to about 5 mg/ml. More particularly, L-alpha phosphatidylcholine may be present in the storage solution from about 0.1 mg/ml to about 7.5 mg/ml, and more typically from about 0.25 mg/ml to about 5 mg/ml.

Oxidative phosphorylation may also be promoted by including non-essential amino acids in the synthetic storage medium. For example, non-essential amino acids from about 0.5 mM to about 14 mM may be present in the storage solution, or about 1.0 mM to about 10 mM. More particularly, L-alanine from about 0.5 mM to about 14 mM may be present in the storage solution, or from about 1.0 mM to about 10 mM.

The synthetic storage solution may also contain unsaturated free long chain fatty acids to promote oxidative phosphorylation. The storage solution described herein may contain from about 0.05 mM to about 1.5 mM of contain unsaturated free long chain fatty acids, or about 0.1 mM to about 1 mM. More particularly the storage medium may contain palmitic acid from about 0.05 mM to about 1.5 mM, or about 0.1 mM to about 1 mM.

As noted above, the storage solutions described above may be used as a "stand-alone" storage medium substantially free of plasma. However, more preferably, a platelet storage medium described herein may also include a selected concentration of plasma. The percentage of plasma is calculated by the equation: $X/(X+Y)\cdot 100\%$=Percentage of Plasma. X represents the starting volume of the platelet fraction (platelets in plasma) before resuspension and Y represents the volume of synthetic media (e.g. solution) added to the platelet fraction. If a higher percentage of plasma is desired it may be added to either the starting platelet fraction, the synthetic medium, or the final resuspended platelets and a similar calculation may be used to calculate the percentage plasma. For instance, if $X_1$ is the volume of the platelet fraction (platelets in plasma) and $X_2$ is the volume of added plasma, the total percentage of plasma is calculated with the equation: $(X_1+X_2)/(X_1+X_2+Y)\cdot 100\%$=Percentage of Plasma.

The plasma may be supplied by the residual plasma contained in the platelet rich fractions which are resuspended with storage medium. In addition, and if necessary, plasma may also be added to the storage medium. Thus, if five fractions of buffy coat platelets (platelets in plasma) each having a volume of about 15 ml are pooled and combined with 300 ml of synthetic medium then the percentage of plasma in the suspension ready for storage is calculated $(5\times15)/[(5\times15)+300]\cdot100\%=20\%$. Similarly, if five fractions of buffy coat platelets (platelets in plasma) each having a volume of about seven (7) ml are pooled and combined with 300 ml of synthetic medium then the percentage of plasma in the suspension ready for storage is calculated $(5\times7)/[(5\times7)+300]\cdot100\%=10.4\%$.

The relative amount of plasma that may be present in the storage medium described herein will preferably be less than about 40%. More preferably, plasma may be present from about 8% to about 24%, and most preferably from about 10% to about 20%.

Further reduction in plasma concentration may also be possible. Thus in other embodiments, plasma may be present in the storage medium in amount of less than 10%, such as, from about 0.5% to about 10%, or from about 1% to about 9%. In other embodiments plasma may be present in the storage medium from about 2% to about 8%, or from about 3% to about 7%, or from about 4% to about 6%.

The storage media allows the stored platelets to preserve functionality and viability upon transfusion to a patient for between about 2 to about 15 days, or between about 4 to about 13 days, or even between about 5 to about 10 days. Typically, the storage media allows the stored platelets to preserve functionality and viability upon transfusion to a patient for more than about 5 days, or for more than about 7-8 days, including up to nine (9) days Storage medium disclosed herein may be also used in conjunction with methods of photodecontamination of platelets as described, for example, in U.S. Pat. No. 5,908,742 which is herein incorporated by reference in its entirety.

By way of example, but not limitation, illustrations of methods of collecting and storing platelets using the storage media described herein are provided below.

Example 1

The partitioning of the ingredients of the synthetic storage solution may consist of 2 parts-part 1, a neutral buffered physiological compartment containing one set of components such as the citrate, acetate, phosphate, sodium ion and optionally magnesium ion, calcium ion and potassium ion, and part 2, an acidic carbohydrate compartment containing the dextrose, and optionally calcium ion, magnesium ion and potassium ion with both compartments having similar osmolarity. In Table 1 an example of a synthetic media with two compartments is presented.

TABLE 1

Composition of platelet storage solution in a three bag assembly (in g/Liter):

Buffered Physiological Compartment

| | |
|---|---|
| Bag 1 containing (in g/L) | 275 ml |
| Na$_3$Citrate•2H$_2$O | 3.21 |
| Na Acetate 3H$_2$O | 4.45 |
| NaH$_2$PO$_4$•2H$_2$O | 0.382 |
| Na$_2$HPO$_4$ | 1.109 |
| KCl | 0.407 |
| NaCl | 4.43 |
| pH | 7.0-7.4 |
| Osmolarity | 300 mOsm/L |
| Bag 2 containing (in g/L) | 25 ml |

Carbohydrate Compartment

| | |
|---|---|
| Dextrose Monohydrate | 40 |
| CaCl$_2$•2H$_2$O | 0 or 1.76 |
| MgCl$_2$•6H$_2$O | 3.66 |
| pH | 4-6 |
| Osmolarity | 292 or 328 mOsm/L |
| Bag 3: final storage container (PL146) | |

FIG. 2 shows each compartment separately stored in a sterile bag with the carbohydrate compartment having a volume of 25 ml in bag 2 and the buffered physiological compartment having a volume of 275 ml in bag 1. The compartments may be combined by passage ways such as tubing to allow mixing of the compartments to form the synthetic medium in bag 3. Alternatively each bag 1 and bag 2 could be individually connected to bag 3 and the compartments mixed in bag 3.

Once combined, the storage solution described herein and shown in Table 1 (in 300 mL volume) may contain, for example, approximately 16.8 mM dextrose monohydrate (D-glucose), 0 or 1.0 mM calcium chloride, 1.5 mM magnesium chloride, 10 mM sodium citrate, 30 mM sodium acetate, sodium 9.4 mM phosphate (7.2 mM dibasic sodium phosphate anhydrous and 2.2 mM monobasic sodium phosphate dihydrate), 5 mM potassium chloride and 69.55 mM sodium chloride. This aqueous storage solution may then be combined with the platelet product containing residual plasma to yield a platelet product or suspension for storage with a desired plasma ratio for instance from about 10% to about 20%. Some methods of preparing platelets such as apheresis type collection or methods that involve washing steps may result in high concentrations of platelets with relatively small volumes of plasma. Consequently, in some cases, resuspension of the platelets for storage may require the addition of plasma as well as synthetic media. In addition the medium may include 1 μM of acetyl-L-carnitine.

Study to Evaluate Platelet Storage Media

A study was conducted to evaluate the in vitro storage parameters of platelet concentrates stored in various platelet storage (or additive) solutions (i.e., PAS) with a plasma ratio reduced to about 20%. The comparison was made against platelets stored in 100% plasma.

a. Composition of Platelet Storage Media

The study was a paired study consisting of five (5) study arms, as shown in Table 2. The compositions of the different proposed storage solutions are described in Tables 3a and 3b below in grams/liter and mmol/liter, respectively.

TABLE 2

| | |
|---|---|
| Arm 1: | Plasma 100% |
| Arm 2 | Plasma 20%/InterSol |
| Arm 3: | Plasma 20%/InterSol + dextrose & magnesium (PSM1) |
| Arm 4 | Plasma 20%/PAS - 0 mM calcium (PSM2) |
| Arm 5 | Plasma 20%/PAS - 1 mM calcium (PSM3). |

TABLE 3a

Formulations of PAS Solutions (gram/liter)

| | Study Arm | | | |
|---|---|---|---|---|
| | 2 | 3 | 4 | 5 |
| | Name of PAS Solution | | | |
| | InterSol | PSM1 | PSM2 | PSM3 |
| Na$_3$Citrate2H$_2$O | 3.18 g/L | 2.92 g/L | 2.937 g/L | 2.937 g/L |
| NaAcetate3H$_2$O | 4.42 g/L | 4.06 g/L | 4.076 g/L | 4.076 g/L |
| NaH$_2$PO$_4$•2H$_2$O | 1.05 g/L | 0.96 g/L | 0.349 g/L | 0.349 g/L |
| Na$_2$HPO$_4$ anhydrous | 3.05 g/L | 2.80 g/L | 1.015 g/L | 1.015 g/L |
| NaCl | 4.52 g/L | 4.15 g/L | 4.0696 g/l | 4.056 g/L |
| KCl | — | — | 0.372 g/l | 0.372 g/l |
| Dextrose monohydrate | | 3.28 g/L | 3.328 g/l | 3.328 g/l |
| Magnesium Chloride hexahydrate | | 0.300 g/L | 0.3045 g/L | 0.3045 g/L |
| Calcium Chloride dihydrate | — | | | 0.1464 g/l |
| Volume PAS storage solution added to each platelet pool | 280 ml | 305 ml | 300 ml | 300 ml |

TABLE 3b

Concentrations of Solutes in PAS solutions (mmole/liter)

| | Study Arm | | | |
|---|---|---|---|---|
| | 2 | 3 | 4 | 5 |
| | Name of PAS Solution | | | |
| | InterSol | PSM1 | PSM2 | PSM3 |
| $Na_3Citrate2H_2O$ | 10.8 mM | 9.93 mM | 9.985 mM | 9.985 mM |
| $NaAcetate3H_2O$ | 32.5 mM g/L | 29.8 mM | 29.956 mM | 29.956 mM |
| $NaH_2PO_4 \cdot 2H_2O$ | 6.73 mM | 6.17867 mM | 2.240 mM | 2.240 mM |
| $Na_2HPO_4$ anhydrous | 21.5 mM | 19.7 mM | 7.151 mM | 7.151 mM |
| NaCl | 77.3 mM | 71.0 mM | 69.64 mM | 69.41 mM |
| KCl | — | — | 4.99 mM | 4.99 mM |
| Dextrose monohydrate | — | 16.5 mM | 16.79 mM | 16.79 mM |
| Magnesium Chloride hexahydrate | — | 1.475 mM | 1.50 mM | 1.50 mM |
| Calcium Chloride dihydrate | — | — | — | 0.996 mM |

PSM2 = PAS with 0.44 mL added NaCl 0.9% (total volume 300.44 mL)
PSM3 = PAS with 0.44 mL added $CaCl_2$ 2 H2O 100 mg/mL (total volume 300.44 mL)

b. Evaluation of Storage Media

In vitro platelet data collected during the course of the study was compared at the end of the nine (9) day shelf life with the EU requirements listed in Table 4.

TABLE 4

Storage Parameters

| Parameters | Desirable Range at the end of the recommended Shelf life |
|---|---|
| pH (22° C.) | 6.4-7.4 corrected for 22° C. (a) |
| Volume | >40 mL per 60 × $10^9$/single unit equivalent (b) |
| Platelet content | >60 × $10^9$/single unit equivalent (b) |

(a) Guide to the preparation, use and quality assurance of blood components - 13th edition, 2007
(b) These criteria were evaluated considering the samplings done through storage In addition, the different test media were evaluated for in vitro parameters as described below. All in vitro data collected from day 1 to day 9 were analyzed using a two-way analysis of variance (ANOVA) with repeated measure factor (Day) to determine significant difference between the 5 groups of platelet concentrates (Medium). The Day*Medium interaction is shown in Figures. In the figures, the vertical bars denote the 0.95 confidence interval.

c. Selection of Donors

Selection of volunteer donors was based on local standard practices. Only regular blood donors that fulfill the Swedish requirements for blood donation and have given their informed consent were included in the study.

d. Study Design i. Preparation of Leuko-Filtered Platelet Concentrates-Preparation of Buffy Coats for Test and Control Platelets Blood units of 450 ml±10% were collected from volunteer donors in 63 ml CPD anticoagulant solution using quadruple blood containers. Whole blood units were processed on the same day. High speed centrifugation was applied according to the local standard procedure. Buffy coats with a reduced volume of plasma (about 15 mL [considering a pool of 5 buffy coats samples, and about 300 mL platelet additive solution]) were separated from plasma and red cells. The buffy coat units were kept overnight at room temperature.

For each experiment, 25 buffy coats (BCs) were pooled using the Fenwal Transfer pack Code R4R2041, well mixed and then divided into five equal parts (one for each of the study arms) from the same ABO compatible pool of buffy coats.

The nine (9) day study was repeated eight times such that a total of 40 Platelet Concentrates were prepared. For each of the prepared platelet concentrates, the weight of the pooled BCs diluted with a platelet storage solution was determined, by subtracting the tare weight of the pooling bag from the weight of filled pooling container. The net volume of pool of buffy coats (BC) was calculated using the formula: Net volume of BC pool Net Weight Pooled BC(g)/1.04 g/mL.

An alternate method to determine the total volume of the pooled buffy coats diluted with a platelet storage solution, when using the OrbiSac procedure, is to add the volume of the 5 buffy coat samples to the volume of a platelet storage solution. The volume of the five buffy coats being may be obtained by recording the weight of the 5 pooled buffy coats and calculating the net volume of the 5 BCs using the formula:

Net volume (V1 in mL) of the pool of 5 BCs=net weight of 5 BCs(g)/1.06 g/mL.

ii. Preparation of Pooled Buffy Coats with 100% Plasma or InterSol

Using a sterile docking device and appropriate sterile pooling set a pool of five (5) buffy coats were mixed with either 100% plasma (300 mL) or InterSol (280 mL) to produce Study arm 1 and Study arm 2 respectively.

iii. Preparation of Pooled Buffy Coats with PSM 1 (InterSol+Dextrose & Magnesium), PSM 2 and PSM3 (with Calcium)

Referring to FIG. 2, a cannula 20 was broken on the bottom of Bag 2, allowing the dextrose solution to flow into the empty PL146 Bag 3 through tubing 22. The cannula 24 was broken on the top of Bag 1, allowing the platelet storage solution to flow in the Bag 3, while passing through tubing 26 and the emptied Bag 2. The PSM and dextrose solution were thoroughly mixed in Bag 3.

The dextrose tubing line was heat sealed (as close as possible to the Bag 3; see FIG. 4), and the empty dextrose and PSM bags were detached.

iv. Preparation of a Platelet Storage Solution with or without Calcium

To formulate the solution containing calcium chloride, 0.44 mL of calcium chloride $2H_2O$ at 100 mg/mL was added to the 300 mL platelet concentrates. If no calcium was added, NaCl 0.9% is added (0.44 mL) to maintain osmolarity. For each test unit, appropriate volume of Calcium Chloride dihydrate Injection USP were added (0.44 mL if 100 mg/mL Calcium Chloride dihydrate Injection USP vials supplied) to the container holding Platelets in PSM to give a final concentration of 1 mM Calcium Chloride. For the a platelet storage solution with no calcium added, 0.44 mL of 0.9% NaCl was added under the same conditions. Addition of calcium chloride or saline to the bags was carried out with a 1 mL syringe by injection through the sampling-site, in a laminar flow hood under ultraviolet light, or a Class D room.

Table 5 illustrates an experimental disposable set for an example of the storage solution PSM3 and shows the concentration of the solutes of the storage solution in each bag of a bag set such as that shown in FIG. 2 (both in grams/liter and millimoles/liter). Table 5 also shows the concentrations both in grams/liter and millimoles/liter of the solutes of the storage solution when bag 1 and bag 2 are combined (FIG. 2). Table 5 also provides an example the addition of 0.44 mls of 100 mg/ml $CaCl_2$ dihydrate to the remaining solutes of PSM3 in 300 mls to yield approximately 300.44 mls of PSM3.

TABLE 5

Experimental

| Ingredients | MW | | | Final in 300 ml mM | Final in 300 ml g/L | PSM 3 - add 0.44 mL of 100 mg/ml $CaCl_2$ to 300 mL (total 300.44 mL) | |
|---|---|---|---|---|---|---|---|
| | | | | | | mM | g/L |
| Disposable Bag 2 | | g/L 25 mL | mM 25 mL | | | | |
| Dextrose Monohydrate | 198.16 | 40 | 202 | 16.82 | 3.33 | 16.79679 | 3.328452 |
| $CaCl_2 \cdot 2H_2O$ | 147.02 | 1.76 | 12 | 1.0 | 0.147 | 0.996136 | 0.146452 |
| $MgCl_2 \cdot 6H_2O$ | 203.30 | 3.66 | 18 | 1.5 | 0.305 | 1.50 | 0.304503 |
| Disposable Bag 1 | | g/L/ 275 mL | mM/ 275 mL | | | | |
| $Na_3$ Citrate·2H2O | 294.1 | 3.21 | 11 | 10 | 2.94 | 9.9854 | 2.936693 |
| NaAcetate 3H2O | 136.08 | 4.45 | 33 | 30 | 4.08 | 29.9561 | 4.076421 |
| NaH2PO4, 2H2O | 156.01 | 0.382 | 2 | 2.2 | 0.350 | 2.2402 | 0.349487 |
| Na2HPO4 | 141.96 | 1.109 | 8 | 7.2 | 1.017 | 7.1512 | 1.015178 |
| KCl | 74.55 | 0.407 | 5 | 5 | 0.373 | 4.9927 | 0.372204 |
| NaCl | 58.44 | 4.43 | 76 | 70 | 4.06 | 69.4123 | 4.056454 |

The OrbiSac procedure was used to prepare the platelet concentrates, the prepared platelet concentrates were transferred at the end of the preparation from the Gambro ELP storage bag into the Fenwal PL2410 (reference code R4R7004 or R4R7006) storage bag.

e. Measurement of Study Parameters

The units were tested for the parameters listed below:
Weights (for Volume assessment) at the following test intervals:
   day 1, platelet storage solution (PAS) filled (Wo) and empty (Tare 0)
   day 1, pooled buffy coats with the platelet storage solution (PAS) in the OrbiSac pooling bag (W1)
   day 1, platelet concentrate at time of preparation, before any sampling, in the OrbiSac ELP storage bag: weight W2
   day 1, platelet concentrate at time of preparation, after transfer, in the Fenwal PL2410 storage bag: weight W3
Each day before sampling
Plasma ratio (before any sampling made)
Leukocyte by Nageotte chamber only at day 1
Platelet counts: at time of preparation day 1, then at day 3, day 5, day 7, day 9.
Red Blood Cell (Visual inspection or by Nageotte) at time of preparation (day 1)

The following tests were performed at the following test intervals: at time of preparation (day 1), day 3, day 5, day 7 and day 9.
pH
Swirling
Glucose and lactate concentration
Bicarbonate concentration
adenosine triphosphate (ATP)
Lactate dehydrogenase LDH
partial carbon dioxide pressure $pCO_2$
partial oxygen pressure $pO_2$
CD62P
Hypotonic Shock Response
Mean Platelet Volume
Bacterial control: at Day 9, or earlier if pH falls outside of a particular range or if fibrinogen clots are observed.

The results of the in vitro study were evaluated using appropriate statistical techniques as calculation of means, medians, and standard deviations. Data reflecting the test results of the platelets stored in 100% plasma or the various formulation of PSM (the arms of the study) are presented in FIGS. 3-14 with test being run typically on days 1, 3, 5, 7 and 9.

Figure 4:
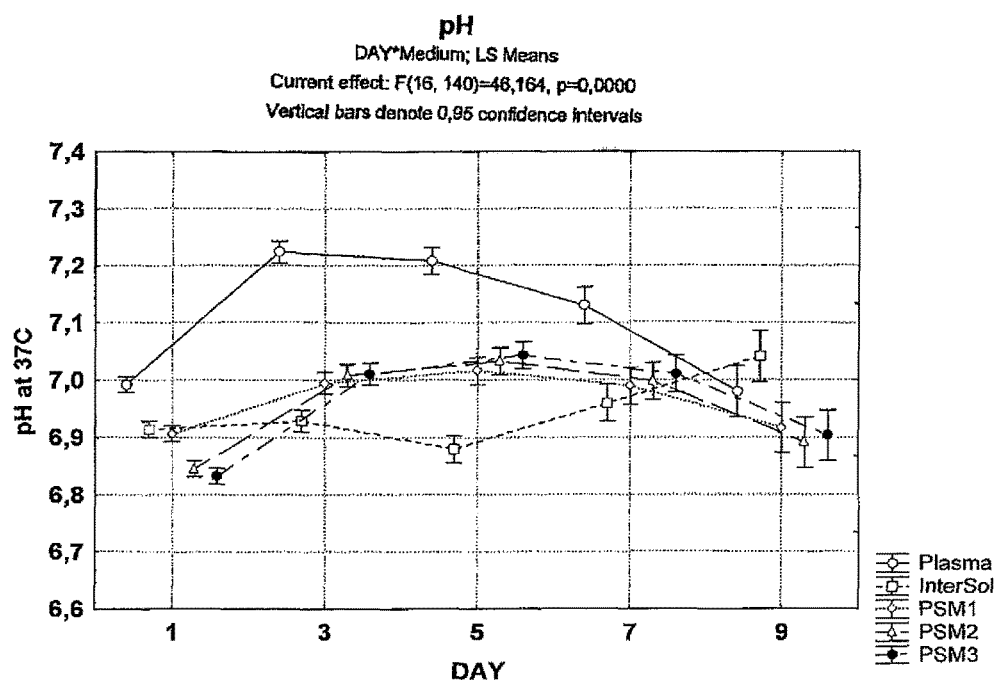
FIG. 4 illustrates graphically the mean pH levels versus days of storage for platelets stored in different storage media.

As illustrated in FIG. 4 the average pH for platelet samples stored in 100% plasma or 20% plasma plus one of the 4 platelet storage solutions, Intersol, PSM1, PSM2, and PSM3, appear to be in an acceptable range, between 6.8 and 7.2 when measured at 37° C. Throughout the nine (9) days of storage, the average pH of samples stored under each of the indicated conditions remained within 0.2 units of the pH measured on the first day of storage. There was no significant difference in the pH between the three PSM arms. The arm containing 100% plasma showed significantly higher average pH values over the study.

Figure 5:
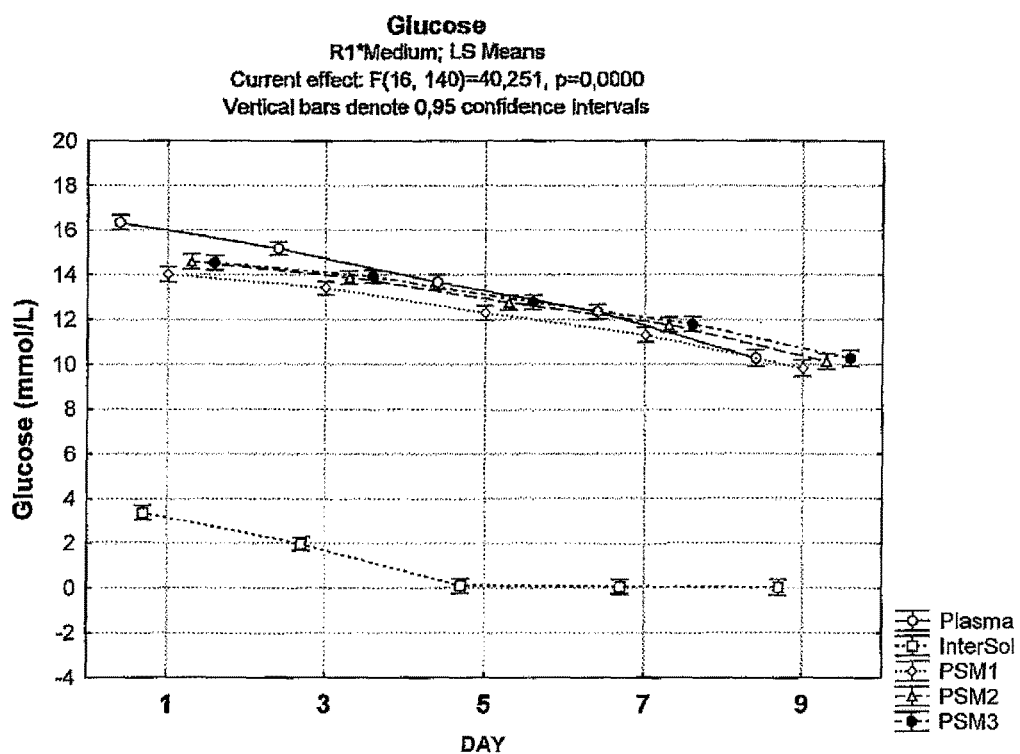
FIG. 5 illustrates graphically the mean glucose levels versus days of storage for platelets stored in different storage media.

As illustrated in FIG. 5, platelet samples stored in 20% plasma and the a platelet storage solutions PSM1, PSM2 and PSM3 all display adequate average glucose levels throughout storage, with levels at day 9 of storage at 22±2° C. comparable to glucose levels found in platelets stored in 100% plasma. In addition, there was significantly lower glucose consumption in the PSM arms compared to plasma. With respect to the PSM arms, there was lower remaining glucose in PSM1 versus PSM2 and PSM3 at day 9.

Taken together FIGS. 4 and 5 indicate that storage of platelets in 20% plasma and each of the a platelet storage solutions PSM1, PSM2 and PSM3, like storage in 100% plasma, provides both control of the pH of storage solution and maintains adequate glucose reserves throughout the nine days of storage at 22±2° C.

Figure 6:
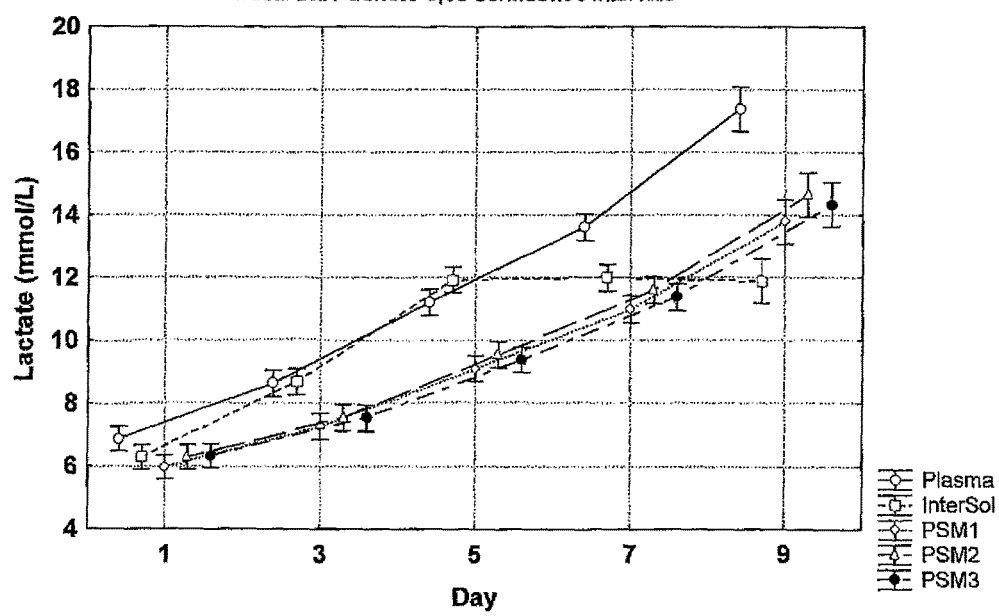
FIG. 6 illustrates graphically the mean lactate levels in mmol/L versus days of storage for platelets stored in different storage media.

As illustrated in FIG. 6, storage of platelets at 22±2° C. in one of the reformulated PAS solutions (PSM1, PSM2 and PSM3) which contain glucose and 20% plasma at 22±2° C. results in average lactate production that does not exceed that observed for platelets stored in 100% plasma and does not exceed the amount of lactate produced by platelets stored in InterSol which does not contain glucose and 20% plasma. The results show that there was no lactate production after day 5 in plasma 20%/InterSol. There was higher production of lactate in Plasma 100% compared to the other arms of the study. There was no significant difference in lactate between the 3 PSM groups until at least day 9 of storage at 22±2 C.

Table 6 summarizes the results for each of the study arms with respect to glucose consumption and lactate production in mmol/day/$10^{11}$ platelets. Glucose consumption and lactate production are significantly lower in PSM1, PSM2 and PSM3 storage media compared to 100% Plasma. The gradual decrease in lactate production in PSM1, PSM2 and PSM3 may suggest a more efficient oxidation of pyruvate and further into oxaloacetate, for use in the TCA cycle.

TABLE 6

| Test arm (N = 8 per arm) | Glucose consumption | Lactate production |
|---|---|---|
| Plasma 100% (day 1-day 9) | 0.075 ± 0.01 | 0.13 ± 0.01 |
| Plasma 20%/InterSol (day 1-day 5) | 0.076 ± 0.01 | 0.13 ± 0.02 |
| Plasma 20%/PSM1 (day 1-day 9) | 0.060 ± 0.01* | 0.11 ± 0.01* |
| Plasma 20%/PSM2 (day 1-day 9) | 0.056 ± 0.01* | 0.11 ± 0.01* |
| Plasma 20%/PSM3 (day 1-day 9) | 0.054 ± 0.00* | 0.10 ± 0.01* |

Figure 7:
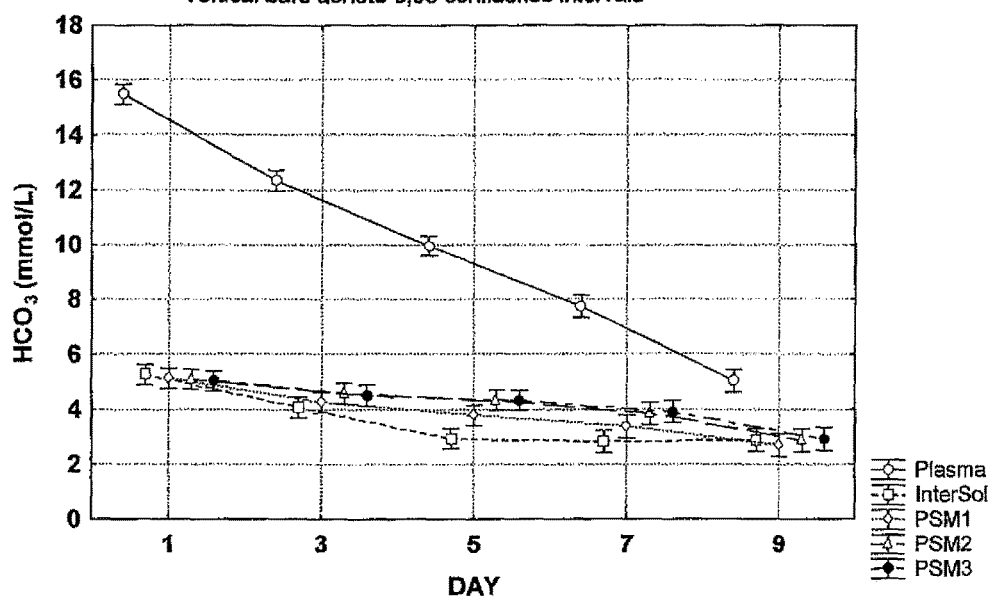
FIG. 7 illustrates graphically the mean bicarbonate levels of the storage solution in mmol/L versus days of storage for platelets stored in different storage media.

As illustrated in FIG. 7, there was a decrease of bicarbonate concentration over the course of the study for the platelets stored in 100% plasma. No such decrease observed in the PSM arms, possibly due to presence of acetate in the storage solution. There was a significant difference between PSM2 or PSM3 and PSM1, with better maintenance of bicarbonate levels in PSM2 or PSM3 versus InterSol or PSM1.

Figure 8:
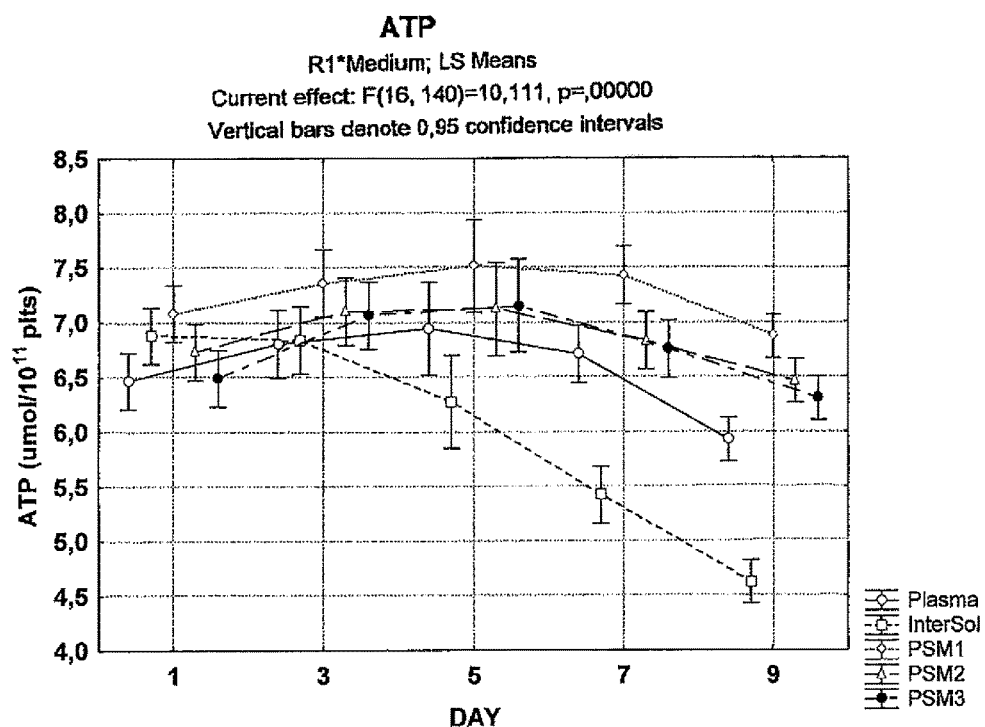
FIG. 8 illustrates graphically the mean ATP levels in $\mu mol/10^{11}$ Plts versus days of storage for platelets stored in different storage media.

As illustrated in FIG. 8, platelet samples stored at 22±2° C. in the reformulated a platelet storage solutions, PSM1, PSM2 and PSM3, with 20% plasma have improved maintenance of average ATP levels as compared to platelets stored in InterSol and 20% plasma. While the average ATP levels in the platelet samples with 20% plasma and a platelet storage solutions are comparable to samples stored in 100% plasma through out the 9 days of storage, the average ATP levels in PSM1, PSM2 and PSM3 exceeded the levels found in the InterSol sample from day 5 through day 9 of storage.

Figure 9:
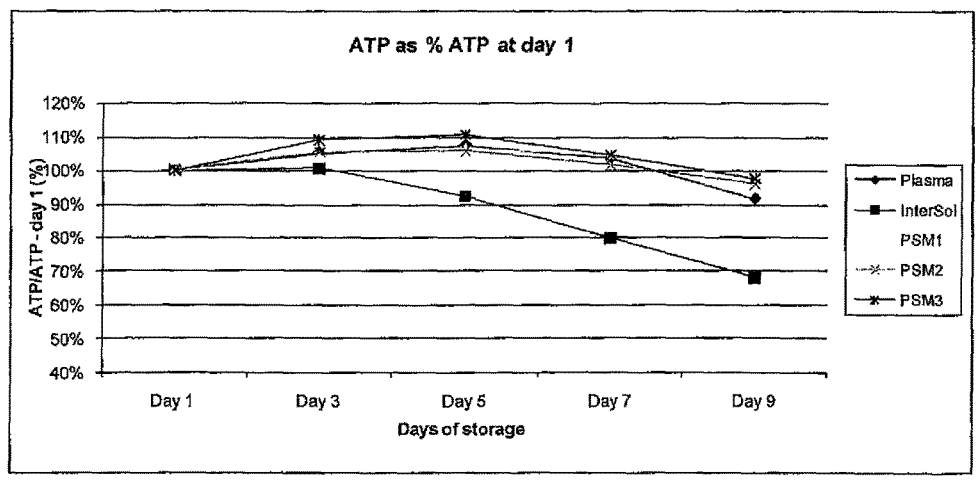
FIG. 9 illustrates graphically the mean ATP levels expressed as a mean percentage of the day 1 ATP values versus days of storage for platelets stored in different storage media.

As shown in FIG. 9 and in tabular form in Table 7, on day 9 of storage the platelets stored in 100% plasma have about 92% of the average ATP level measured on day 1 of storage, and the platelets stored in 20% plasma and any one of PSM1, PSM2 and PSM3 have about 97% of the day 1 ATP levels. The drop in ATP levels by day 5 observed in platelets stored in InterSol plus 20% plasma appears to correlate with the drop in glucose levels observed by day 5 for these samples. (eg see FIG. 5).

TABLE 7

| ATP as % day 1 | Day 1 | Day 3 | Day 5 | Day 7 | Day 9 |
|---|---|---|---|---|---|
| Plasma | 100% | 105% | 107% | 104% | 92% |
| InterSol | 100% | 101% | 93% | 80% | 68% |
| PSM1 | 100% | 104% | 106% | 105% | 97% |
| PSM2 | 100% | 105% | 106% | 102% | 96% |
| PSM3 | 100% | 109% | 111% | 104% | 98% |

Reference Data (n=8 Per Arm)

Figure 10:
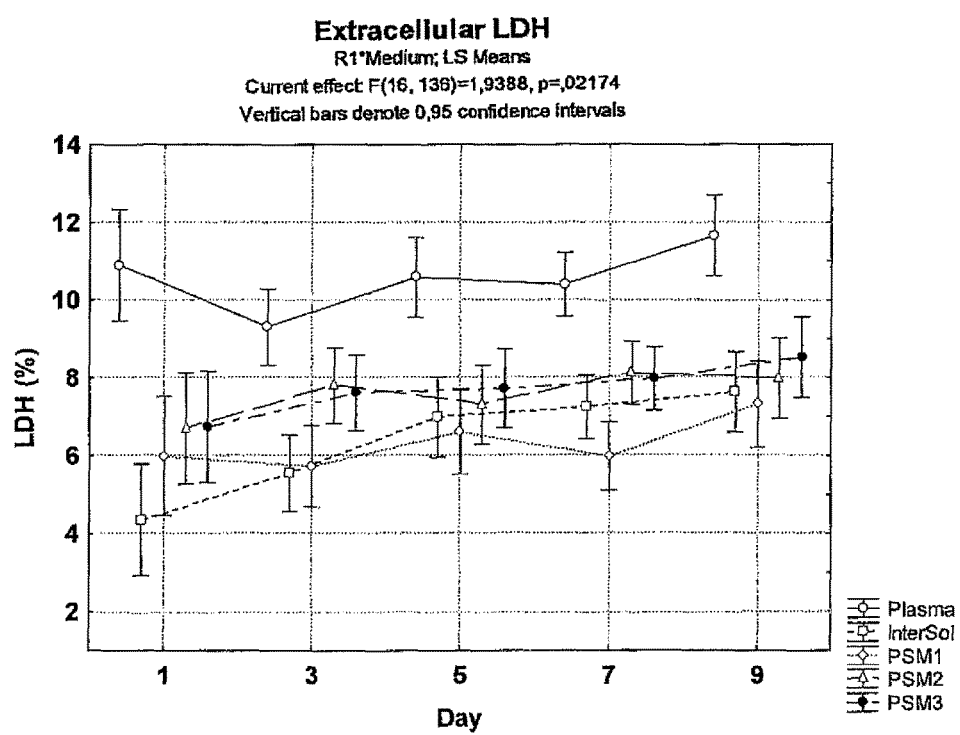
FIG. 10 illustrates graphically the mean extracelluar lactate dehydrogenase levels as a percentage of total lactate dehydrogenase for a particular sample versus days of storage for platelets stored different storage media.

As illustrated in FIG. 10, lower average levels of extracellular lactate dehydrogenase were found in the platelet samples stored at 22±2° C. in a platelet storage solutions PSM1, PSM2 and PSM3 and InterSol each with 20% plasma than were found in platelet samples stored in 100% plasma.

Figure 11:
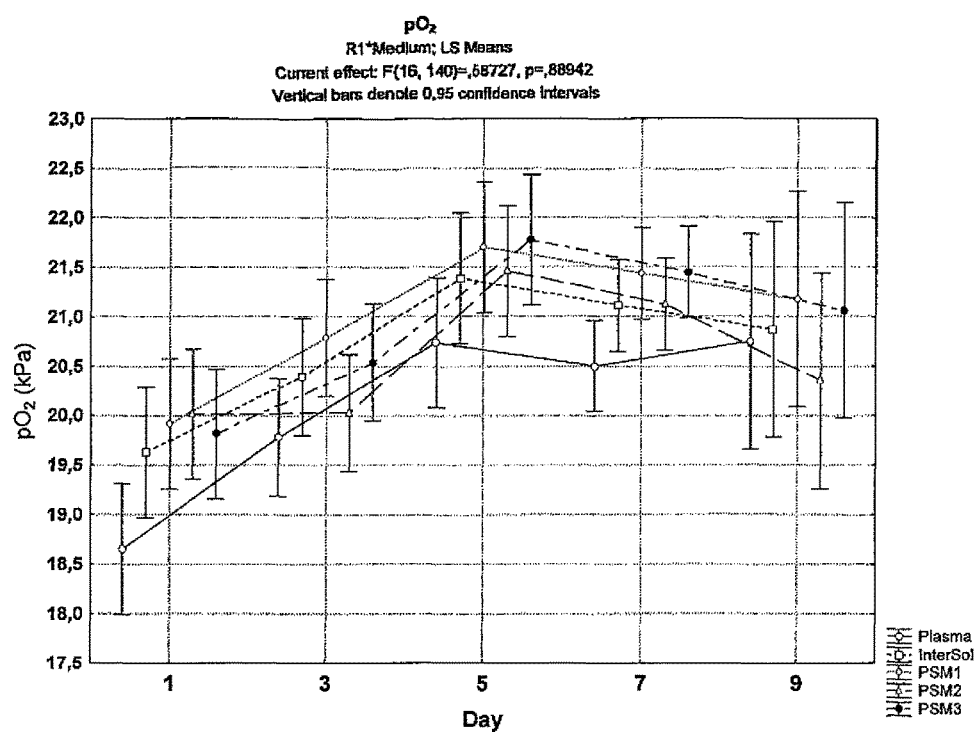
FIG. 11 illustrates graphically the mean $O_2$ concentration of the storage solution as $pO_2$ in kPA versus days of storage for platelets stored in different storage media.

As illustrated in FIG. 11, each storage solution PSM1, PSM2, PSM3 and InterSol with 20% plasma displayed statistically similar oxygen concentrations to 100% plasma throughout the 9 days of storage of platelets at 22±2° C. There was no significant interaction observed between any of the media.

Figure 12:
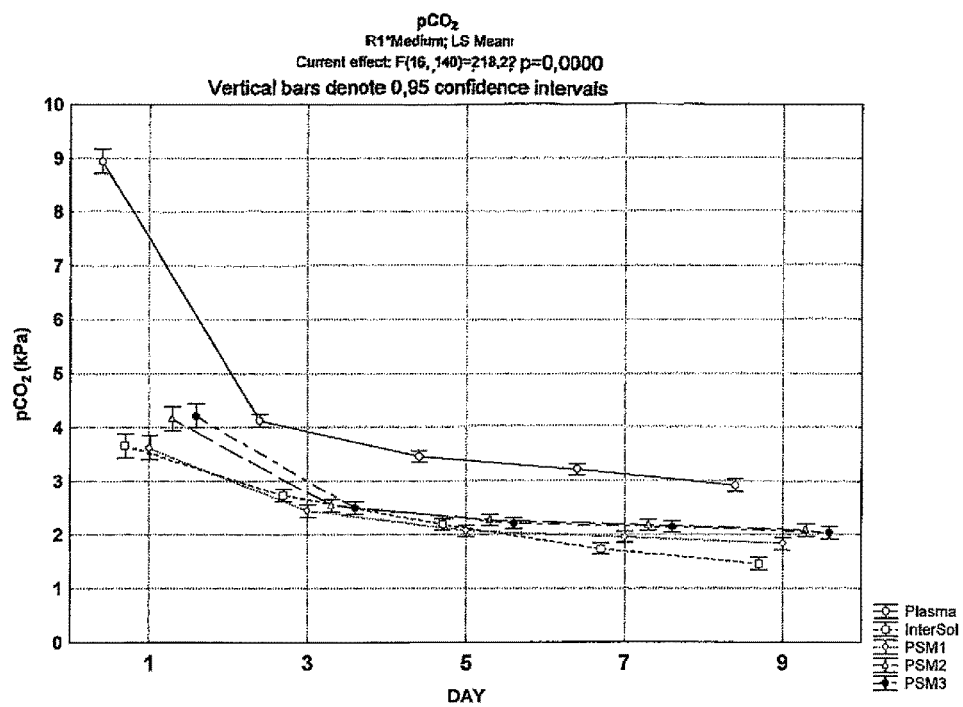
FIG. 12 illustrates graphically the mean $CO_2$ concentration of the storage solution as $pCO_2$ in kPA versus days of storage for platelets stored in different storage media.

As illustrated in FIG. 12, there was a significantly higher pCO2 decrease in the 100% Plasma arm which correlates to the decrease in bicarbonate through storage in plasma (See FIG. 7). There was significantly lower pCO2 concentration in InterSol compared to the 3 PSM arms.

Figure 13:
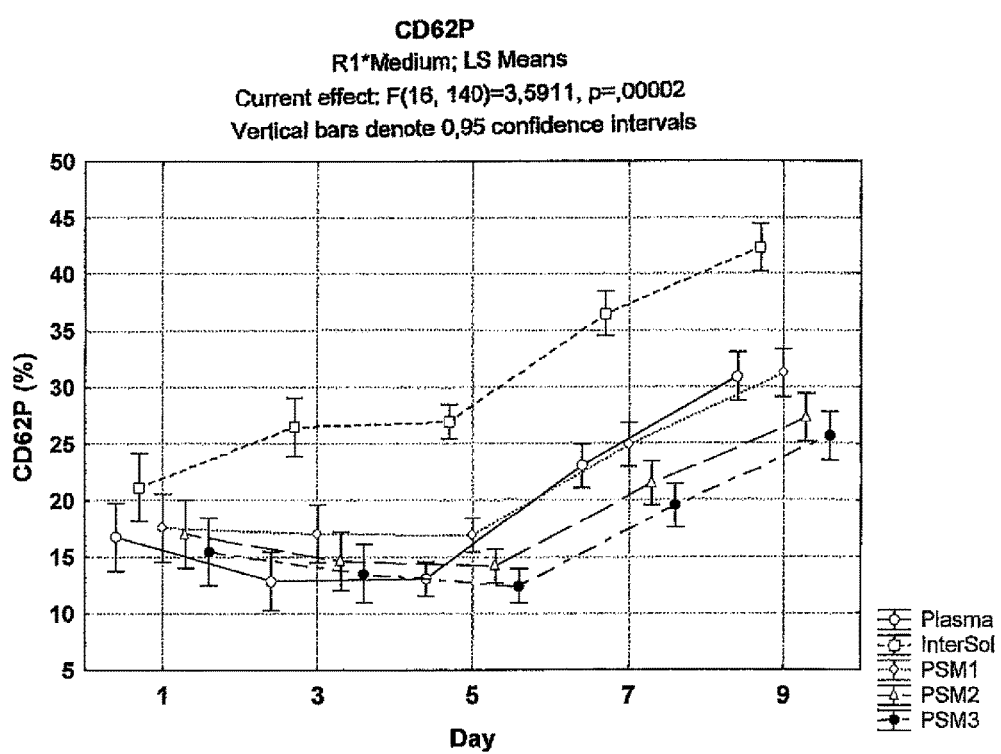
FIG. 13 illustrates graphically platelet expression level of P-selectin as measured by the percentage of platelets reacting with the CD62P antibody versus days of storage for platelets stored in different storage media.

As observed in FIG. 13, the % of platelets expressing CD62P in the PSM2 arm was similar to the % of platelets expressing CD62P in the plasma arm while the % of platelets expressing CD62P in PSM3 was significantly lower than the % CD62P in platelets stored in 100% plasma.

Figure 14:
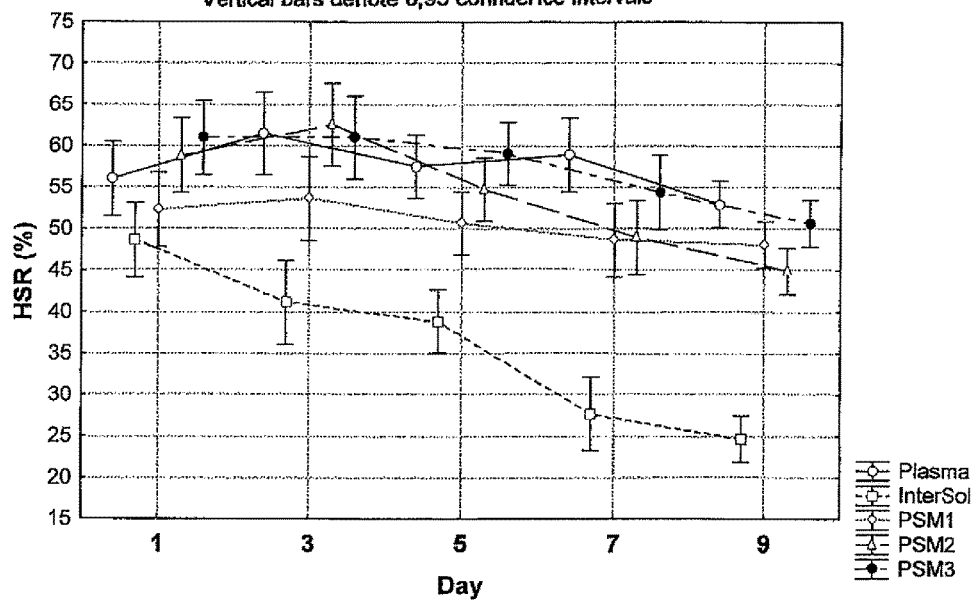
FIG. 14 illustrates graphically the ability of platelets to respond appropriately to hypotonic shock as measured by the mean HSR percentage versus days of storage for platelets stored in different storage media.

As shown in FIG. 14, the storage solution used to store platelets at 22±2° C. appeared to affect the average percentage of platelets that respond appropriately to hypotonic shock as measured by the HSR test. By day 3 of storage, platelets stored in InterSol with 20% plasma or in PSM1 displayed a lower HSR percentage than platelets stored in 100% plasma. There was no significant difference and no interaction in HSR values between PSM3 and plasma. Therefore, the inclusion of $Ca^{2+}$ in storage solutions described herein may allow the storage of platelets in stressed conditions, such as, for example, storage at 4° C. No significant difference but a significant interaction in HSR values between PSM2 and plasma.

As shown in Table 8 below, all samples show normal swirling behavior.

TABLE 8

| | Swirling results | | | | |
|---|---|---|---|---|---|
| | Day | | | | |
| Test Medium | 1 | 3 | 5 | 7 | 9 |
| Plasma 100% | 2 ± 0 | 2 ± 0 | 2 ± 0 | 2 ± 0 | 2 ± 0 |
| Plasma 20%/InterSol | 2 ± 0 | 2 ± 0 | 2 ± 0 | 2 ± 0 | 2 ± 0 |
| Plasma 20%/PSM1 | 2 ± 0 | 2 ± 0 | 2 ± 0 | 2 ± 0 | 2 ± 0 |
| Plasma 20%/PSM2 | 2 ± 0 | 2 ± 0 | 2 ± 0 | 2 ± 0 | 2 ± 0 |
| Plasma 20%/PSM3 | 2 ± 0 | 2 ± 0 | 2 ± 0 | 2 ± 0 | 2 ± 0 |

All samples were negative for bacterial contamination when sampled on day 9 of the study When weighing components, some experimental variability is expected. Use of the terms "about" or "approximately" to reflect this variability. This variability is typically plus or minus 5% and usually less than 10%.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

We claim:

1. A platelet product comprising:
   platelets;
   between about 10%-20% plasma;
   an aqueous storage solution consisting of:
   70 mM±less than 5% sodium chloride;
   10 mM±less than 5% sodium citrate;
   30 mM±less than 5% sodium acetate;
   0.5-3.0 mM±less than 5% magnesium chloride;
   5 mM±less than 5% potassium chloride;
   1.0 mM±less than 5% calcium chloride;
   17 mM±less than 5% glucose; and one or more buffers, one of which is 9.4 mM±less than 5% sodium phosphate buffer containing 7.2 mM±less than 5% $Na_2HPO_4$ and 2.2 mM±less than 5% $NaH_2PO_4.2H_2O$; and
   wherein upon 9 days of storage, said platelet product retains about 98% of its adenosine triphosphate (ATP) content.

2. The platelet product of claim 1 comprising about 20% plasma.

* * * * *